United States Patent [19]

Stapler et al.

[11] Patent Number: 5,300,305

[45] Date of Patent: Apr. 5, 1994

US005300305A

[54] BREATH PROTECTION MICROCAPSULES

[75] Inventors: Judith H. Stapler, Wilmington; Mary A. Hunter, Cincinnati, both of Ohio

[73] Assignee: The Procter & Gamble Company, Cincinnati, Ohio

[21] Appl. No.: 17,944

[22] Filed: Feb. 12, 1993

Related U.S. Application Data

[63] Continuation of Ser. No. 762,530, Sep. 12, 1991, abandoned.

[51] Int. Cl.$^5$ .................... A61K 9/50; A61K 9/16; A61K 9/68

[52] U.S. Cl. ..................... 424/490; 424/48; 424/49; 424/58; 424/435; 424/440; 514/948; 514/963

[58] Field of Search ............... 424/490, 48, 49, 58, 424/435, 440

[56] References Cited

U.S. PATENT DOCUMENTS

| | | | |
|---|---|---|---|
| 2,311,923 | 2/1943 | Lautman | 424/440 |
| 2,446,792 | 8/1948 | Shelton et al. | 260/295 |
| 3,431,208 | 3/1969 | Bailey | 252/106 |
| 3,832,460 | 8/1974 | Kosti | 424/54 |
| 3,911,099 | 10/1975 | DeFoney et al. | 424/435 |
| 3,957,964 | 5/1976 | Grimm | 424/49 |
| 3,962,383 | 6/1976 | Hagiwara et al. | 264/4 |
| 4,039,653 | 8/1977 | DeFoney et al. | 424/481 |
| 4,071,614 | 1/1978 | Grimm | 424/49 |
| 4,169,885 | 10/1979 | Raaf et al. | 424/440 |
| 4,196,189 | 4/1980 | Raaf et al. | 424/440 |
| 4,251,195 | 1/1981 | Suzuki et al. | 425/6 |
| 4,260,596 | 4/1981 | Mackles | 424/440 |
| 4,312,889 | 1/1982 | Melsheimer | 426/86 |
| 4,329,333 | 5/1982 | Barr | 424/49 |
| 4,409,202 | 10/1983 | Witzel et al. | 424/440 |
| 4,422,985 | 12/1983 | Morishita et al. | 264/4.4 |
| 4,426,337 | 1/1984 | Suzuki et al. | 264/4 |
| 4,481,157 | 11/1984 | Morishita et al. | 264/4.1 |
| 4,597,959 | 7/1986 | Barr | 424/49 |
| 4,690,816 | 9/1987 | Hatta et al. | 424/456 |
| 4,695,466 | 9/1987 | Morishita et al. | 424/456 |
| 4,710,384 | 12/1987 | Rotman | 424/465 |
| 4,749,575 | 6/1988 | Rotman | 424/441 |
| 4,762,719 | 8/1988 | Forester | 424/440 |
| 4,765,984 | 8/1988 | Vellekoop et al. | 424/441 |
| 4,800,087 | 1/1989 | Mehta | 424/497 |
| 4,847,090 | 7/1989 | Della Posta et al. | 424/440 |
| 4,857,335 | 8/1989 | Bohm | 424/440 |
| 4,861,268 | 8/1989 | Garay et al. | 424/435 |
| 4,906,488 | 3/1990 | Pera | 424/486 |
| 4,952,402 | 8/1990 | Sparks et al. | 424/440 |
| 5,004,595 | 4/1991 | Cherukuri et al. | 424/440 |
| 5,008,106 | 4/1991 | Merianos et al. | 424/80 |
| 5,013,557 | 5/1991 | Tai | 424/493 |
| 5,064,650 | 12/1991 | Lew | 424/435 |
| 5,084,278 | 1/1992 | Mehta | 424/441 |
| 5,098,725 | 3/1992 | Rotman et al. | 426/98 |
| 5,164,195 | 11/1992 | Lew | 424/490 |
| 5,169,631 | 12/1992 | Rase et al. | 424/401 |

FOREIGN PATENT DOCUMENTS

| | | | |
|---|---|---|---|
| 22662 | 1/1981 | European Pat. Off. | 424/58 |
| 273823 | 7/1988 | European Pat. Off. | 424/58 |
| 0332175 | 9/1989 | European Pat. Off. | |
| 423002 | 4/1991 | European Pat. Off. | 424/59 |
| 2051483 | 4/1971 | France | 424/440 |
| 2570604 | 3/1986 | France | 424/58 |
| 2643261 | 8/1990 | France | 424/58 |
| 89/10117 | 11/1989 | PCT Int'l Appl. | 514/963 |
| 90/02655 | 3/1990 | PCT Int'l Appl. | 514/963 |
| 91/062292 | 5/1991 | PCT Int'l Appl. | 514/951 |
| 1060258 | 3/1967 | United Kingdom | 424/58 |
| 2210889 | 6/1989 | United Kingdom | 424/54 |

*Primary Examiner*—Shep K. Rose
*Attorney, Agent, or Firm*—Douglas C. Mohl; David K. Dabbiere; Jacobus C. Rasser

[57] ABSTRACT

Microcapsules providing breath protection are described and claimed as well as methods of their use.

9 Claims, No Drawings

BREATH PROTECTION MICROCAPSULES

This is a continuation of application Ser. No. 762,530 filed on Sep. 12, 1991, now abandoned.

TECHNICAL FIELD

The present invention relates to oral compositions in the form of microcapsules which provide long lasting breath protection.

BACKGROUND OF THE INVENTION

The use of breath control compositions such as breath mints, mouthwashes, chewing gums, etc. is widespread in most of the developed countries of the world. Another form which has been used are microcapsules containing a flavorant or other breath protection agent. These executions have acceptance due not only to their usefulness away from a place to expectorate mouthwashes but also due to the fact that they can be swallowed when the user does not need any more of the actives or doesn't want it in the mouth any longer.

Although microcapsules have been used, there are problems associated with their manufacture. Often times the wall of the microcapsule may develop imperfections and lose the contents prematurely. Additionally, it may not be possible to easily incorporate breath control actives into the core.

The present inventors have found that by incorporating the breath control actives into the shell of the microcapsule, problems associated with solubility of the actives in core diluents can be avoided.

It is therefore an object of the present invention to provide improved microcapsules.

It is another object of the present invention to provide microcapsules which provide improved breath control.

It is still another object of the present invention to provide improved methods of providing breath control.

These and other objects will become more apparent from the detailed description which follows.

All percentages and ratios used herein are by weight unless otherwise specified. Additionally, all measurements are made at 25° C. unless otherwise specified.

SUMMARY OF THE INVENTION

The present invention in one of its aspects relates to microcapsules which contains breath control actives in the shell of the microcapsule.

DETAILED DESCRIPTION OF THE INVENTION

The essential as well as optional components of the capsules of the present invention are described in the following paragraph.

Capsule Shell Material

The shell material of the microcapsules of the present invention can be any materials which are suitable for ingestion as well as retention in the oral cavity. Materials which are suitable include gelatin, polyvinyl alcohols, waxes, gums and sugar candy type materials used in cough drops and mints, for example.

The shell material is used to form any of a wide variety of shapes such as spheres, oblong shapes, disks, puffed squares and cylinders. The shell thickness is preferably in the range of about 30 um to about 2 mm, preferably from about 70 um to about 110 um. If the microcapsules are spherical, the particle diameter is generally in the range of from about 2 mm to about 9 mm.

Breath Control Actives in the Shell

The breath control actives suitable for inclusion in the shell of the microcapsules are quaternary compounds such as pyridinium salts (e.g., cetyl pyridinium chloride), other cationic materials such as chlorhexidine salts, zinc salts, surfactants such as sodium lauryl sulfate, salts such as sodium laurate, chlorophyl, copper compounds such as copper gluconate and sweeteners such as sugars, corn syrups, saccharin and aspartame.

The breath control agents are generally used in an amount of from about 0.01% to about 5%, preferably from about 0.3% to about 0.4% of the weight of the wall material or from about 0.001% to about 2%, preferably from about 0.04% to about 0.06% of the total weight of the capsule.

Agent Suitable for Use in the Core of Capsule

The open core of the microcapsules of this invention may contain any number of additional materials to provide additional efficacy and/or sensory perceptions. Such agents may include flavoring agents such as thymol, eucalyptol, menthol, methyl salicylate or witch hazel. These agents are used in an amount of from about 0.1% to about 25%, preferably from about 10% to about 15% of the total capsule weight.

In addition, a variety of sweetening agents such as those mentioned above for inclusion in the shell may also be included in the core. These agents are used in an amount of from about 0.1% to about 5%, preferably from about 0.35% to about 0.5% of the total capsule weight.

In addition to the above components, organic diluents may be included with the core materials. Preferred are oils such as corn, olive, rapeseed, sesame, peanut or sunflower. These are used in an amount of from about 20% to about 80%, preferably from about 65% to about 70% of the total capsule weight.

Method of Manufacture

The capsules of the present invention can be made using a variety of techniques. One method is described after the following examples.

INDUSTRIAL APPLICABILITY

The capsules of the present invention are used by placing the capsules into the mouth and retaining them therein for a period sufficient to provide the desired effect.

The following examples further describe and demonstrate preferred embodiments within the scope of the present invention. The examples are given solely for the purposes of illustration and are not to be construed as illustrative of limitations of this invention. Many variations thereof are possible without departing from the invention's spirit and scope.

EXAMPLES 1-4

The following compositions/capsules are representative of the present invention.

| Component | 1 | 2 | 3 | 4 |
|---|---|---|---|---|
| | Weight % | | | |
| Gelatin | 12.578 | 12.328 | 12.578 | 17.578 |

-continued

| Component | 1 | 2 | 3 | 4 |
|---|---|---|---|---|
| Sorbitol Sol'n (70% Aqueous) | 2.046 | 2.05 | 2.046 | 2.046 |
| Saccharin | 0.372 | 0.500 | 0.372 | 0.450 |
| FD&C Blue #1 | 0.002 | 0.002 | 0.002 | — |
| FD&C Yellow #5 | 0.002 | — | 0.002 | 0.004 |
| Captex 300[1] | 72.200 | 70.00 | 71.925 | 66.142 |
| Flavor | 12.750 | 15.00 | 12.75 | 13.500 |
| Cetyl Pyridinium Chloride | 0.045 | — | — | — |
| Domiphen Bromide | 0.005 | — | — | — |
| Chlorhexidine | — | 0.12 | — | — |
| $ZnCl_2$ | — | — | 0.025 | — |
| Sodium Lauryl Sulfate | — | — | 0.300 | — |
| Triclosan | — | — | — | 0.28 |

[1]Captex 300 is a triglyceride supplied by Capitol City Product, Columbus, Ohio.

The above compositions are prepared by mixing the components of the core in one container and the components of the shell in another container. The shell materials are heated to provide a fluid medium. The core and shell materials are then pumped separately to a two-fluid nozzle submerged in an organic carrier medium. The capsules formed are allowed to cool and stiffen. They are then denatured and separated for further handling.

In the above compositions any of a wide variety of other shell materials, breath control agents, sweeteners as well as other components.

What is claimed is:

1. Microcapsules adapted to be placed and retained in the mouth, and which are suitable for providing breath protection comprising a core, or center fill, into which it may not be possible to easily incorporate breath control actives, which core or center fill includes from about 20% to about 80% of the total capsule weight of oil or triglyceride core diluent, said core containing from about 0.1% to about 25% of the total capsule weight of flavoring agents providing additional efficacy and/or sensory perceptions, and a shell material, surrounding said core or center fill, suitable for retention in the oral cavity as well as for ingestion, and disposed within said shell material, from about 0.001% to about 2% of the total weight of the capsule, one or more breath control actives whose solubility may present problems in said oil or triglyceride core diluent, said microcapsules not being incorporated into breath mints, mouthwashes, chewing gums, or other breath control or oral hygiene compositions.

2. Microcapsules according to claim 1 wherein the shell material is selected from the group consisting of polyvinyl alcohol, gelatin, waxes, gums and sugar candies.

3. Microcapsules according to claim 2 wherein the breath control agent is selected from the group consisting of quaternary ammonium compounds, other cationic agents, zinc salts, surfactants, sodium laurate, chlorophyl, copper compounds, flavors and sweeteners.

4. Microcapsules according to claim 3 wherein the microcapsule is in the form of a sphere, oblong, disk, a puffed square, or a cylinder.

5. Microcapsules according to claim 4 wherein the microcapsules are in the form of spheres.

6. Microcapsules according to claim 5 wherein the microcapsules are from about 2 mm to about 9 mm in diameter and the shell wall thickness is from about 30 um to about 2 mm.

7. Microcapsules according to claim 6 wherein the shell material is gelatin and the breath control active is triclosan.

8. A method of reducing breath odor in the mouth wherein capsules according to claim 1 are placed in the mouth and left therein for a time sufficient to provide a benefit.

9. A method according to claim 8 wherein the microcapsule shell is made of gelatin.

* * * * *